(12) United States Patent
Cascella et al.

(10) Patent No.: US 12,090,334 B2
(45) Date of Patent: Sep. 17, 2024

(54) AUTOMATED EXTERNAL DEFIBRILLATION WITH DEEP NEURAL NETWORK

(71) Applicant: Defibtech, LLC, Guilford, CT (US)

(72) Inventors: Alicia Cascella, Southbury, CT (US); Matt Valentine, Madison, CT (US); Shirin Hajeb Mohammadalipour, Vernon, CT (US); Ki Chon, Mansfield, CT (US)

(73) Assignees: DEFIBTECH, LLC, Guilford, CT (US); THE UNIVERSITY OF CONNECTICUT, Farmington, CT (US)

( * ) Notice: Subject to any disclaimer, the term of this patent is extended or adjusted under 35 U.S.C. 154(b) by 544 days.

(21) Appl. No.: 17/384,079

(22) Filed: Jul. 23, 2021

(65) Prior Publication Data

US 2022/0032075 A1    Feb. 3, 2022

Related U.S. Application Data

(60) Provisional application No. 63/057,950, filed on Jul. 29, 2020.

(51) Int. Cl.
*A61N 1/39*      (2006.01)
*G06N 3/04*      (2023.01)
(Continued)

(52) U.S. Cl.
CPC .......... *A61N 1/39044* (2017.08); *G06N 3/04* (2013.01); *G06T 7/0012* (2013.01); *G16H 20/30* (2018.01);
(Continued)

(58) Field of Classification Search
None
See application file for complete search history.

(56) References Cited

U.S. PATENT DOCUMENTS

2009/0315889 A1   12/2009   Tognola
2011/0190839 A1   8/2011    Vaisnys
2020/0085333 A1   3/2020    Freed et al.

OTHER PUBLICATIONS

Hannun AY, Rajpurkar P, Haghpanahi M, Tison GH, Bourn C, Turakhia MP, Ng AY. Cardiologist-level arrhythmia detection and classification in ambulatory electrocardiograms using a deep neural network. Nat Med. Jan. 2019;25(1):65-69 (Year: 2019).*

(Continued)

*Primary Examiner* — Ankit D Tejani
(74) *Attorney, Agent, or Firm* — Davis Malm D'Agostine PC; David J. Powsner

(57) ABSTRACT

The invention provides, in some aspects, an automated external defibrillator (AED) that includes defibrillation circuitry capable of delivering a therapeutic shock to a patient. The AED also includes an input that receives a patient ECG signal representing real-time electrical activity of a heart of the patient and that may include artifacts resulting from cardiopulmonary resuscitation of the patient. The AED generates a real-time alert from a patient data image that is based on the patient ECG signal to effect application of the therapeutic shock to the patient. The AED generates that alert based at least in part on a shock recommendation of an artificial intelligence (AI) engine that analyzes the patient data image using a machine learning (ML) model trained with training data images. The patient data image comprises pixels whose values are a function of magnitudes of components of representations of respective time-slices of the patient ECG signal in a frequency domain. At least one training data image comprises pixels whose values are a function of magnitudes of components of representations of (Continued)

respective time-slices of a respective training ECG signal in the frequency domain.

20 Claims, 6 Drawing Sheets

(51) Int. Cl.
*G06T 7/00* (2017.01)
*G16H 20/30* (2018.01)
*G16H 30/40* (2018.01)
*G16H 50/20* (2018.01)

(52) U.S. Cl.
CPC .............. *G16H 30/40* (2018.01); *G16H 50/20* (2018.01); *G06T 2207/20081* (2013.01); *G06T 2207/20084* (2013.01); *G06T 2207/30048* (2013.01)

(56) References Cited

OTHER PUBLICATIONS

Oh SL, Ng Eyk, Tan RS, Acharya UR.. Automated diagnosis of arrhythmia using combination of CNN and LSTM techniques with variable length heart beats. Comput Biol Med. Nov. 1, 2018:102:278-287 (Year: 2018).*

Search Report and the Written Opinion of the International Searching Authority issued in PCT/US2021/043078 on Jan. 11, 2021.

* cited by examiner

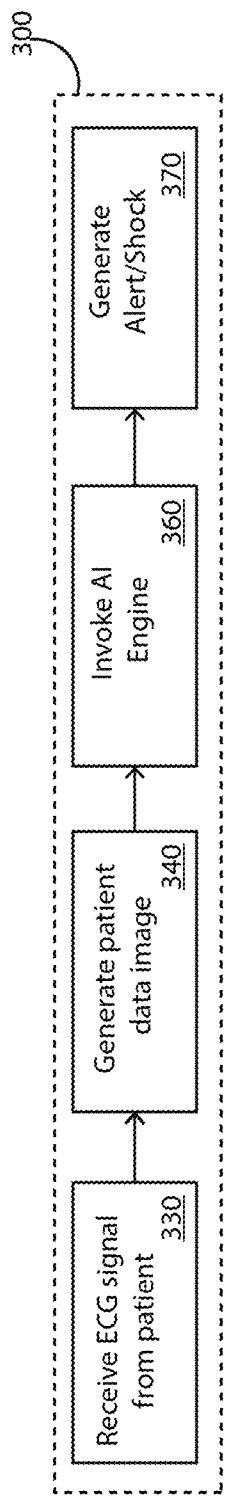
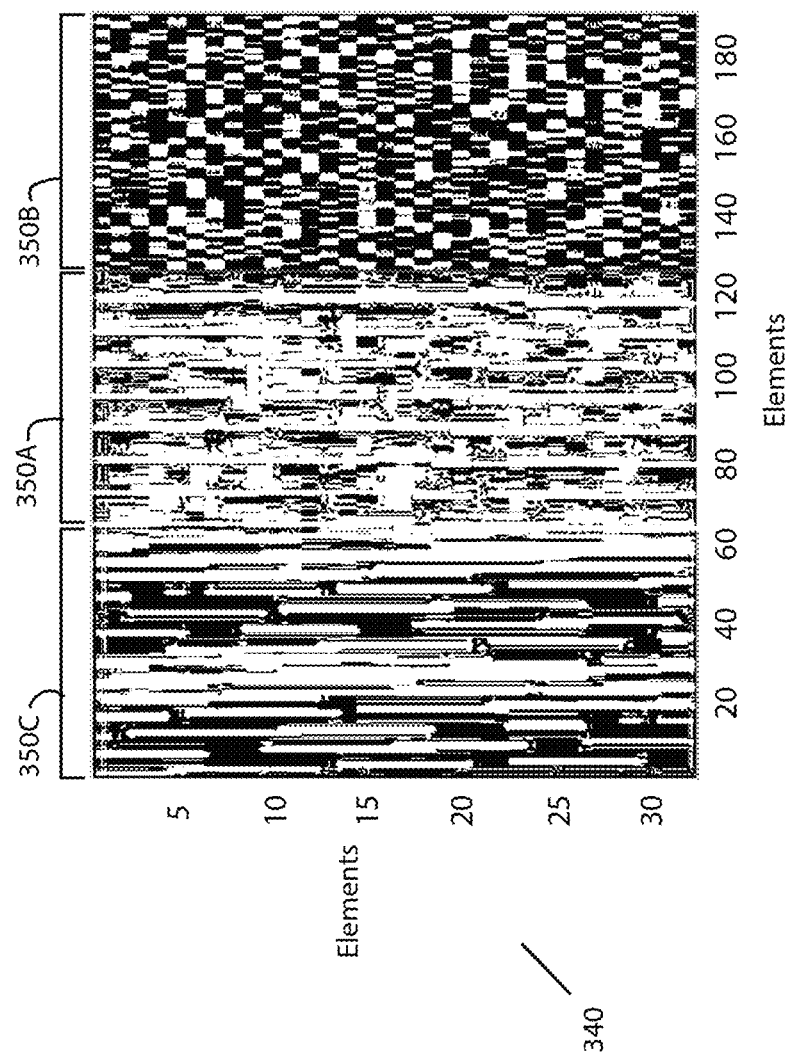

AUTOMATED EXTERNAL DEFIBRILLATION WITH DEEP NEURAL NETWORK

REFERENCE TO RELATED APPLICATION

This application claims the benefit of priority of U.S. Provisional Patent Application Ser. No. 63/057,950, filed Jul. 29, 2020, entitled "Deep Neural Network Approach for Continuous Electrocardiogram-based Shock Advisory System During Cardiopulmonary Resuscitation," the teachings of which are incorporated herein by reference.

BACKGROUND OF THE INVENTION

The invention pertains to automated external defibrillation and, more particularly, by way of example, to methods and apparatus for automated external defibrillation based on deep neural networks. The invention has application, inter alia, in automated external defibrillation during cardiopulmonary resuscitation (CPR).

Hundreds of thousands of Americans die from cardiac arrest each year, the majority away from the hospital. Immediate high quality cardiopulmonary resuscitation (CPR) can improve the survival rate in the event of an out-of-hospital cardiac arrest (OHCA). Electrical defibrillation can reestablish regular heart beats, and its early application along with continuous CPR can lead to a return of spontaneous circulation while minimizing long-term health consequences.

The decision by a first responder or other health care provider on whether and when to deliver a defibrillating electrical shock depends on the near real-time analysis of an electrocardiogram (ECG). However, accurately deciphering the rhythms derived from ECG during CPR is challenging because chest compressions induce large artifacts in ECG waveforms. To overcome this, the prior art includes teachings instructing the responder/provider to pause delivery of CPR during hearth rhythm analysis. Those pauses, which can last from several seconds to nearly one-half minute, can not only lead, for example, to brain damage from oxygen deprivation, they can also affect the likelihood of survival. Minimizing, if not eliminating those pauses, is therefore desirable.

The prior art has made numerous attempts at analyzing heart rhythms during CPR delivery. Those attempts can be categorized into two different approaches. The first uses signal processing techniques to filter CPR-related artifacts from ECG signals, and the second attempts direct analysis of the corrupted ECG signal during CPR.

An object of the invention is to provide improved methods and apparatus for health care including, by way of example, automated external defibrillation.

Another object is to provide such improved methods and apparatus for use in connection with cardiopulmonary resuscitation (CPR).

A further object of the invention is to provide such methods and apparatus for health care including, by way of example, automated external defibrillation systems.

SUMMARY OF THE INVENTION

AED Using "Data Images" with Pixels Whose Values are Based on ECG Signal Characteristics The foregoing are among the objects attained by the invention, which provides in some aspects an automated external defibrillator (AED) that includes defibrillation circuitry capable of delivering a therapeutic shock to a patient. The AED also includes an input that receives a patient ECG signal representing real-time electrical activity of a heart of the patient and that may include artifacts resulting from cardiopulmonary resuscitation of that patient. The AED generates a real-time alert to effect application of the therapeutic shock to the patient. The AED generates that alert based at least in part on a shock recommendation of an artificial intelligence (AI) engine that analyzes a patient data image using a machine learning (ML) model trained with training data images. The patient data image is a matrix which is treated (at least in part) as an image and whose elements are treated as pixels of that image, where those elements (and corresponding pixels) have values that are based on the patient ECG signal and, more particularly, that are a function of magnitudes of components of representations of respective time-slices of the patient ECG signal in a frequency domain. At least one training data image likewise comprises pixels whose values are a function of magnitudes of components of representations of respective time-slices of a respective training ECG signal in the frequency domain. References herein to the AI engine and model as independent units within the AED, as in the discussion immediately above, is without loss of generality and includes integral combinations of those units, in whole or in part.

Related aspects of the invention provide an AED, e.g., as described above, wherein the patient data image comprises pixels whose values are a function of phases of the components of the representations of the respective time-slices of the patient ECG signal in the frequency domain, and wherein one or more of the training data images comprises pixels whose values are a function of phases of the components of the respective representations of the respective time-slices of the training ECG signal in that domain.

Further related aspects of the invention provide an AED, e.g., as described above, wherein the patient data image comprises pixels whose values are a function of amplitudes of respective sampled values of a representation of the patient ECG signal in a time domain, and wherein one or more of the training data images comprises pixels whose values are a function of amplitudes of respective sampled values of a representation of the respective training ECG signal in the time domain.

Still further related aspects of the invention provide an AED, e.g., as described above, wherein the patient data image is made up of a plurality of regions, each comprising at least a two-dimensional collection of 500 or more pixels and, preferably, of 1000 or more pixels and, still more preferably, of 2000 or more pixels, where the plurality of regions include at least two and, preferably at least three, of (a) a region comprising pixels whose values are a function of magnitudes of components of representations of respective time-slices of the patient ECG signal in the frequency domain, (b) a region comprising pixels whose values are a function of phases of the components of the representations of the respective time-slices of the patient ECG signal in the frequency domain, (c) a region comprising pixels whose values are a function of amplitudes of respective sampled values of the representation of the patient ECG signal in the time domain; and, wherein one or more of the training data images is made up of a plurality of regions, each comprising at least a two-dimensional collection of 500 or more pixels and, preferably, of 1000 or more pixels and, still more preferably, of 2000 or more pixels, where the plurality of regions includes at least two of (a) a region comprising pixels whose values are a function of magnitudes of respective components of representations of respective time-slices of a respective training ECG signal in the frequency domain, (b) a region comprising pixels whose values are a function of phases of the respective components of the respective representation of the respective time-slice of the respective training ECG signal in that frequency domain, (c) a region comprising pixels whose values are a function of amplitudes of respective sampled values of a representation of the respective training ECG signal in the time domain.

AED with AI Engine and Machine Learning Model Trained from Summed Time Series

Related aspects of the invention provide an AED, e.g., as described above, in which at least one training ECG signal is derived from a summation of (i) a time series of ECG data collected from a subject who was not undergoing CPR when that data was collected, and (ii) a time series of ECG data collected from a subject in asystole and undergoing CPR when that data was collected, which training ECG signal represents ECG data as if collected from the subject undergoing CPR while not in asystole.

Further aspects of the invention provide an AED, e.g., as described above, that includes defibrillation circuitry capable of delivering a therapeutic shock to a patient. The AED also includes an input that receives a patient ECG signal representing real-time electrical activity of a heart of the patient and that may include artifacts resulting from cardiopulmonary resuscitation of the patient. The AED generates a real-time alert from a patient data image that is based on the patient ECG signal to effect application of the therapeutic shock to the patient. The AED generates that alert based at least in part on a shock recommendation of an AI engine that analyzes the patient data image using a machine learning (ML) model trained with training data sets, at least one of which training sets is derived from a summation of (i) a time series of ECG data of collected from a subject who was not undergoing CPR during a time interval when that data was collected, and (ii) a time series of ECG data collected from that or another subject who was in asystole and who was undergoing CPR when that data was collected, which training ECG signal represents ECG data as if collected from the subject undergoing CPR while not in asystole.

Still further aspects of the invention provide an AED e.g., as described above, wherein the ML model is trained using (a) a first plurality of training data sets derived from a said summation in which the training ECG data is collected from subjects whose hearts were in a shockable rhythm, and (b) a second plurality of training data sets derived from a said summation in which the ECG data was collected from subjects whose hearts were not in a shockable rhythm.

Yet still further aspects of the invention provide an AED, e.g. as described above, in which each the summation training data set is 5-15 seconds in length.

AED with Deep Neural Network

Related aspects of the invention provide an AED, e.g., as described above, wherein the AI engine generates the alert based on a shock recommendation of a deep neural network (DNN) that includes a plurality of convolution layers.

Further aspects of the invention provide an AED that includes defibrillation circuitry capable of delivering a therapeutic shock to a patient. The AED also includes an input that receives a patient ECG signal representing real-time electrical activity of a heart of the patient and that may include artifacts resulting from cardiopulmonary resuscitation of the patient. The AED generates a real-time alert from a patient data image that is based on the patient ECG signal to effect application of the therapeutic shock to the patient. The AED generates that alert based at least in part on a shock recommendation of an artificial intelligence (AI) engine comprising a deep neural network (DNN) that includes a plurality of convolution layers and that generates the recommendation using a machine learning (ML) model trained with training data images. The patient data image comprises pixels whose values are a function of a representation of the patient ECG signal. At least one training data image comprises pixels whose values are a function of a representation of a respective training ECG signal.

Related aspects of the invention provide an AED, e.g., as described above, in which the DNN includes a bidirectional long short-term memory (biLSTM) layer in sequence with the convolution layers.

In further related aspects, the invention provides such an AED that further includes a residual connection layer in sequence with the convolution layers and the biLSTM layer.

Still further related aspects of the invention provide an AEU, e.g., as described above, comprising plural residual blocks, each including multiple convolutional layers.

Methods of Automated External Defibrillation Using Data Images with Pixels Whose Values are Based on ECG Signal Characteristics Other aspects of the invention provide methods of automated external defibrillation that include receiving a patient ECG signal representing real-time electrical activity of a heart of a patient and that may include artifacts resulting from cardiopulmonary resuscitation of the patient. A patient data image is generated from pixels whose values are a function of magnitudes of components of representations of respective time-slices of the patient ECG signal in a frequency domain. The methods further include generating a real-time alert to effect application of a therapeutic shock to the patient. That generating step includes determining an efficacy of applying such a shock by analyzing the patient data image with an artificial intelligence (AI) engine and a machine learning (ML) model trained with training data images whose pixel values are a function of magnitudes of components of representations of respective time-slices of respective training ECG signals in the frequency domain.

Related aspects of the invention provide methods of automated external defibrillation, e.g., as described above, comprising generating the patient data image with pixels whose values are a function of phases of the components of the representation of the respective time-slices of the patient ECG signal in the frequency domain. According to related aspects, the generating step includes using, to analyze the patient data image, training data images that likewise comprise pixels whose values are a function of phases of the respective components of the respective representations of the respective time-slices of the respective training ECG signals in the frequency domain.

Further related aspects of the invention provide methods of automated external defibrillation, e.g., as described above, comprising generating the patient data image with pixels whose values are a function of amplitudes of respective sampled values of a representation of the patient ECG signal in a time domain. According to related aspects of the invention, the generating step includes using, to analyze the patient data image, training data images that also comprise pixels whose values are a function of amplitudes of respective sampled values of representations of the respective training ECG signals in the time domain.

Still further related aspects of the invention provide methods of automated external defibrillation, e.g., as described above, comprising generating the patient data image with a plurality of regions, each comprising at least a two-dimensional collection of 500 or more pixels and, preferably, 1000 or more pixels and, still more preferably, 2000 or more pixels, where the plurality of regions includes at least two and, preferably at least three, of (a) a region comprising pixels whose values are a function of magnitudes of components of the representation of the respective time-slices of the patient ECG signal in the frequency domain, (b) a region comprising pixels whose values are a function of phases of the components of the representation of the respective time-slices of the patient ECG signal in the frequency domain, (c) a region comprising pixels whose values are a function of amplitudes of respective sampled values of the representation of the patient ECG signal in the time domain.

According to related aspects of the invention, the generating step includes using, to analyze the patient data image, training data images that comprise a plurality of regions, each comprising at least a two-dimensional collection of 500 or more pixels and, preferably, 1000 or more pixels and, still more preferably, 2000 or more pixels, where the plurality of regions includes at least two of (a) a region comprising pixels whose values are a function of magnitudes of respective components of the representation of respective time-slices of a respective training ECG signal in the frequency domain, (b) a region comprising pixels whose values are a function of phases of the components of the respective representation of the respective time-slices of the respective training ECG signal in the frequency domain, (c) a region comprising pixels whose values are a function of amplitudes of respective sampled values of a representation of the respective training ECG signal in the time domain.

Methods of Automated External Defibrillation Using Artificial Intelligence and Machine Learning Model Trained from Summed Time Series Related aspects of the invention provide methods of training the ML model used in automated external defibrillation, e.g., as described above, from training ECG signals that are summations of (i) time series of ECG data collected from respective subjects who were not undergoing CPR when that respective data was collected, and (ii) time series of ECG data collected from the same or other subjects who were in asystole and who were undergoing CPR when that respective data was collected, which ECG signals represent ECG data as if collected from the respective subject undergoing CPR while not in asystole.

Further aspects of the invention provide methods of training an automated external defibrillator (AED) of the type that includes (i) defibrillation circuitry capable of delivering a therapeutic shock to a patient and (ii) an input that receives a patient ECG signal representing real-time electrical activity of a heart of the patient and that may include artifacts resulting from cardiopulmonary resuscitation of the patient.

The methods include generating a plurality of training ECG signals by summing (i) time series of first ECG data collected from respective subjects who were not undergoing CPR when that respective data was collected, and (ii) time series of second ECG data collected from respective subject who were in asystole and were undergoing CPR when that respective data was collected, which training ECG signals represent the first ECG data as if collected from the respective subjects while undergoing CPR.

The methods further include generating training data images from respective training ECG signals, where each training data image includes pixels whose values are a function of magnitudes of components of a representation of respective time-slices of the respective training ECG signal in a frequency domain.

The methods also include training a machine learning (ML) model of an artificial intelligence (AI) engine using the training data images, where that training step includes identifying whether each such training data image is shockable or not shockable, depending on a corresponding condition of the respective subject from whom was collected the ECG data used in summation of the ECG signal from which that image was generated.

Methods of Automated External Defibrillation with Deep Neural Network

Related aspects of the invention provide methods of automated external defibrillation, e.g., as described above, wherein the generating step includes analyzing the patient data image with a deep neural network (DNN) that includes a plurality of convolution layers.

Other aspects of the invention provide methods of automated external defibrillation that include (i) receiving a patient ECG signal representing real-time electrical activity of a heart of a patient and that may include artifacts resulting from cardiopulmonary resuscitation of the patient, and (ii) generating a patient data image with pixels whose values are a function of magnitudes of components of representations of respective time-slices of the patient ECG signal in a frequency domain. The methods further include generating a real-time alert to effect application of a therapeutic shock to the patient. That generating step includes determining an efficacy of applying such a shock by analyzing the patient data image with deep neural network trained with training data images whose pixel values are a function of magnitudes of respective components of representations of respective time-slices of the respective training ECG signals in the frequency domain.

Related aspects of the invention provide methods of automated external defibrillation, e.g., as described above, in which the generating step includes analyzing the patient data image with a deep neural network that includes a bidirectional long short-term memory (biLSTM) layer in sequence with the convolution layers.

Further related aspects of the invention provide methods of automated external defibrillation, e.g., as described above, in which the generating step includes analyzing the patient data image with a deep neural network that includes a residual connection layer in sequence with the convolution layers and the biLSTM layer.

Still further related aspects of the invention provide methods of automated external defibrillation, e.g., as described above, in which the generating step includes analyzing the patient data image with a deep neural network that includes plural residual blocks, each including multiple convolutional layers.

Still further aspects of the invention provide methods of training a machine learning models for use in health care apparatus, e.g., an automated external defibrillator, in accord with the above.

Yet still further aspects of the invention provide health care devices that utilize artificial intelligence and machine learning models trained using data sets that comprise summations of time series or other data sets.

BRIEF DESCRIPTION OF THE DRAWINGS

A more complete understanding of the invention may be attained by reference to the drawings, in which

FIG. 2 depicts a method executed by the AED of FIG. 1 for automated shock/alert delivery;

FIG. 3 depicts a patient data image of the type generated during execution of the method of FIG. 2;

DETAILED DESCRIPTION OF THE ILLUSTRATED EMBODIMENT

Automated External Defibrillator

Figure 1:
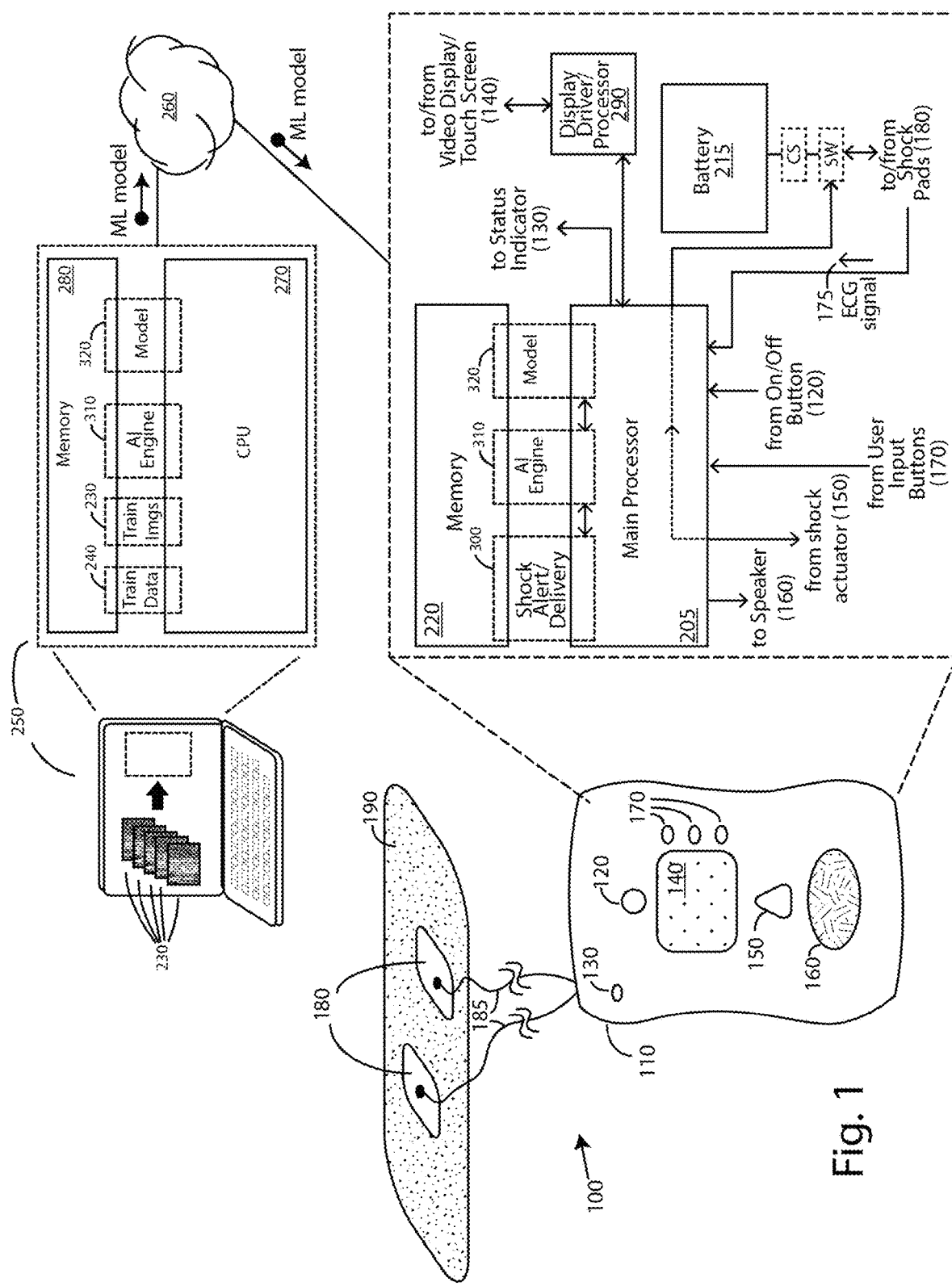
FIG. 1 depicts an automated external defibrillator (AED) according to one practice of the invention.

FIG. 1 depicts an automated external defibrillator (AED) 100 according to one practice of the invention using artificial intelligence (AI) to effect application of the defibrillating (or "therapeutic") shock to a patient, e.g., via an alert to the AED's human operator. It will be appreciated the form factor of the AED shown in FIG. 1 is merely by way of example and that the invention can be practiced with AEDs of other form factors known in the art as adapted in accord with the teachings hereof.

Turning to the drawing, AED 100 includes a housing 110 on which an on/off button 120, display 140, shock delivery actuator 150, and speaker 160 may be operationally disposed, all per convention in the art as adapted in accord with the teachings hereof. Further, the AED 100 may include a status indicator 130 and user interface/control buttons 170, as shown, again, per convention in the art as adapted in accord with the teachings hereof. In addition to supporting the display of information, display 140 may be a touch screen supporting user input, per convention in the art as adapted in accord with the teachings hereof.

AED 100 is coupled to defibrillation shock pads 180 of the type commercially available in the art as adapted in accord with the teachings hereof. In addition to operating under the control (and power) of the AED to deliver a defibrillating or other therapeutic shock to the chest 190 or other portion of a patient (e.g., an actual or apparent heart attack victim) via leads 185, the pads 180 allow the AED to sense electrical activity within patient's chest, all per convention in the art as adapted in accord with the teachings hereof.

That activity is represented by electrical signals passed by the pads 180 to the AED 100 via leads 185, or otherwise, and conditioned per convention in the art by circuitry (not shown) within the AED 100 or external thereto for noise reduction, voltage/current normalization, and otherwise, to form electrocardiogram (ECG) signals of the type known in the art (as adapted in accord with the teachings hereof) that represent the real-time electrical activity of the patient's heart and that may include artifacts resulting from cardiopulmonary resuscitation, if the patient is undergoing such when the AED is sensing heart activity.

AED 100 operates per convention in the art as adapted in accord with the teachings hereof to administer a defibrillation shock to the patient 190. Thus, for example, when the AED 100 is turned on, the main processor 205 (discussed below) may drive speaker 160 and/or display 140 to issue audio and/or visual instructions, respectively, to the AED operator on how to apply the pads to the patient 190 and how to initiate a shock using the shock delivery actuator 150. Once the pads 180 have been applied to the patient, the shock delivery actuator 150 may be pressed, sending an electrical charge from battery 215 through the defibrillation pads 180, and, in turn, normalizing the heart rhythm of the patient.

AED 100 includes circuitry and other internal components, as indicated by the breakout drawing at the right of FIG. 1. This includes a main processor 205, which can comprise a general- or special-purpose microprocessor or other logic device of the type known in the art configured for controlling the AED per convention in the art, as adapted in accord with the teachings hereof. Processor 205 of the illustrated embodiment is coupled to the on/off button 120, the speaker 160, an AED direct current battery 215, the status indicator light 130, memory 220, the user input buttons 170 and, by way of display driver/processor 290, the display/touch screen 140, all per convention in the art as adapted in accord with the teachings hereof; other embodiments may utilize other components instead or in addition, again, per convention in the art as adapted in accord with the teachings hereof.

Charging circuitry (CS), powered by AED battery 215, of the illustrated embodiment is coupled to the shock pads 180 via a switch SW controlled by main processor 205 and/or shock delivery actuator 150, as shown in the drawing, per convention in the art as adapted in accord with the teachings hereof. In some embodiments, the switch SW can be closed, e.g., by pressing of actuator 150, thus, causing the pads to deliver a charge to the patient. In other embodiments, the main processor 205 can effect closure of the switch (e.g., when the AI engine 310 recommends delivery of a shock) or block such closure (e.g., when the AI engine 310 recommends otherwise), as discussed elsewhere herein. The charging circuitry CS can include a voltage step-up and capacitor, or otherwise, all as per convention in the art as adapted in accord with the teachings hereof. In some embodiments, switch SW is implemented in an H-Bridge that is connected to the capacitor of the charging circuitry CS, and a patient safety relay or switch (not shown) is additionally provided, all as per convention in the art as adapted in accord with the teachings hereof.

Processor 205 of the illustrated embodiment is a programmable microprocessor, instructions and data for execution by which are maintained in memory 220, which may comprise any or a combination of random-access memory (RAM), flash memory, solid state or inertial disks, or otherwise, all per convention in the art as adapted in accord with the teachings hereof. This can include, by way of non-limiting example, instructions (and data) supporting shock alert/delivery (element 300), comprising an AI engine (element 310), and comprising a machine learning (ML) model (element 320), all for analyzing patient ECG signals received from the pads 180 and effecting shock delivery as discussed below and elsewhere herein. Storage of such instructions within memory 220 and their transfer to and use by the processor 205 to control the AED 100 consistent herewith is within the ken of those skilled in the art in view of the teachings hereof. In some embodiments, the engine 310 and model 320 are independent, interoperable components within the AED 100. In other embodiments, the engine and model (whether or not identified as such) are integrally combined, in whole or in part, to define a ML-trained and/or ML-trainable artificial intelligence. The illustration of and reference to the AI engine 310 and model 320 as independent units, as immediately above and elsewhere herein, is without loss of generality and includes integral combinations of those units, in whole or in part.

Data stored in memory 220 can also include, by way of non-limiting example, the patient ECG signal 175 that represents real-time electrical activity of the heart of the patient and that may include artifacts resulting from cardiopulmonary resuscitation of the patient. That signal 175 is digitized and converted into a time series of values (e.g., in a vector or other data structure) prior to processing by the AED.

It will be appreciated that the internal and external components of AED 100 shown in the drawing and described herein are by way of example, and that AEDs of other embodiments may employ different components instead or in addition consistent with the teachings hereof. Thus, by way of non-limiting example, some "fully-automatic" embodiments forego a shock delivery actuator 150 and rely instead, on main processor 205 to effect closure of the switch SW, e.g., when the AI engine 310 recommends delivery of a shock.

Shock Alert/Delivery

FIG. 2 depicts steps 300 executed by AED 100 under control of main processor 205 for automated shock/alert delivery and, more particularly, for use of the artificial intelligence (AI) engine 310 and machine learning (ML) model 320 to automatically analyze ECG signals 175 received from the pads 180 to predict if it would be efficacious to deliver a defibrillating shock to the patient— e.g., on account of the patient being in ventricular fibrillation (VF), pulseless ventricular tachycardia (VT), or other "shockable" rhythm—and, if so, to alert the operator in real-time to stand clear of the patient and to press the actuator 150 to deliver the therapeutic shock. In some embodiments, the AED 100 can simply signal the operator to stand clear and can deliver the shock in real-time automatically by closing switch SW, if/when a shockable ECG rhythm is detected. Likewise, the AED 100 avoids generating such alerts (and applying such shocks) when the ECG signal indicates that delivery of a shock would not be efficacious, i.e., when the patient 190 is non-shockable, e.g., is experiencing normal sinus rhythm (NSR), atrial fibrillation (AF), sinus bradycardia (SB), supraventricular tachycardia (SVT), heart block, idioventricular and premature ventricular contractions (PVCs), and so forth. In some embodiments, the actions by AED 100 in steps 300 vis-à-vis alerting the operator, delivering a shock, and/or avoiding same can be based solely on the prediction/recommendation of the engine 310. In other embodiments, that prediction/recommendation is one factor in a decision by the AED 100 to so act; other factors can include the time elapsed since the last shock and the charge on the capacitor in charging circuitry CS, all by way of non-limiting example and all as is within the ken of those skilled in the art in view of the teachings hereof.

In the illustrated embodiment, steps 300 are implemented by way of instructions/data stored in memory 220 and executed on processor 205 (as denoted in FIG. 1), all per convention in the art as adapted in accord with the teachings hereof. In other embodiments, one or more of the steps may be executed in a special-purpose processor or other logic that is separate from processor 205 but that is in communications coupling therewith, e.g., via a backplane bus or otherwise, all as is within the ken of those skilled in the art in view of the teachings hereof.

In step 330, the processor 205 receives the patient ECG signal 175 in real-time from pads 180, i.e., substantially concurrently with occurrence and detection of the electrical activity (in the chest of the patient) represented by the signal 175. In some embodiments, that signal is received by the processor 205 directly via leads 185 to which the pads 180 are attached, while in others the ECG signal 175 is buffered in memory 220 prior to retrieval by processor 205. In the illustrated embodiment, the signal 175 is conditioned digitized and converted to a time series (all per convention in the art as adapted in accord with the teachings hereof) prior to receipt by processor 205; though, in other embodiments, processor 205 may perform one or more of those steps upon receipt of the signal 175.

Patient Data Image Generation

In step 340, the processor 205 generates a patient data image from the patient ECG signal received in step 330. As used herein, a data image is matrix which is treated (at least in part) as an image and whose cells (or elements) are treated as pixels of that image.

Such a patient data image 340 is depicted in FIG. 3. It includes a region 350A comprising a two-dimensional collection of pixels whose values are a function of magnitudes of components of representations of respective time-slices of the patient ECG signal 175 in the frequency domain—and, more particularly, a two-dimensional collection of pixels, each of whose respective values is a function of a magnitude of a respective component of a frequency-domain representation of a respective time-slice that ECG signal. In the illustrated embodiment, the function is the identity function, though, in other embodiments the function can be a scaling or normalization function that ensures the pixel values remain within an acceptable range (e.g., 0-255, or otherwise). Representation of the ECG signal in the frequency domain can be achieved via a Fourier transform (though, other transforms known in the art can be used instead or in addition), with each respective frequency component in that domain having an associated magnitude (and phase), per convention in the art as adapted in accord with the teachings hereof.

The patient data image 340 also includes a region 350B also comprising a two-dimensional collection of pixels. The values of those pixels, however, are a function of phases of the aforesaid components of the representations of the respective time-slices of the patient ECG signal 175 in the frequency domain—and, more particularly, a two-dimensional collection of pixels, each of whose respective values is a function of the phase of the respective component of the frequency-domain representation of the respective time-slice of that ECG signal. As above, in the illustrated embodiment, the function is the identity function, though, in other embodiments the function can be a scaling or normalization function that ensures the pixel values remain within an acceptable range (e.g., 0-255, or otherwise).

The patient data image, moreover, includes a region 350C comprising two-dimensional collection of pixels whose values are a function of amplitudes of respective sampled values (or "samples") of the representation of the patient ECG signal 175 in the time domain—and, more particularly, a two-dimensional collection of pixels, each of whose respective values is a function of the amplitude of the respective sample of the time-domain representation of that ECG signal. In some embodiments, that time-domain representation is the time-series representation of the ECG signal itself and the amplitudes are values of the respective elements of that time series. In other embodiments, the amplitudes are resampled, interpolated and/or extrapolated from that time series, as is within the ken of those skilled in the art in view of the teachings hereof. As above, in the illustrated embodiment, the function is the identity function, though, in other embodiments the function can be a scaling or normalization function that ensures the pixel values remain within an acceptable range (e.g., 0-255, or otherwise).

In the illustrated embodiment, the regions 350A-350C are of like sizes, each being 500 or more pixels and, preferably, of 1000 or more pixels and, still more preferably, of 2000 or more pixels; however, other embodiments may vary in these regards. And, although FIG. 3 is shown in black & white, it will be appreciated that this is for reproducibility and that grayscale and/or color images may more suitably represent the range and variation of pixel values in the respective regions 350A-350C.

Moreover, although the patient data image 340 of the illustrated embodiment includes three regions defined as above, the patient data image 340 of other embodiments may include only a single such region, e.g., 350A, while that of still other embodiments may utilize that region in combination of one of the other two, i.e., 350E or 350C, and/or still other collections of pixels based on the patient ECG signal. Still further, although the image 340 and regions 350A-350C of the illustrated embodiment are in two dimensions, in still other embodiments the image and/or regions may be in three or more dimensions.

EXAMPLE

Figure 4:
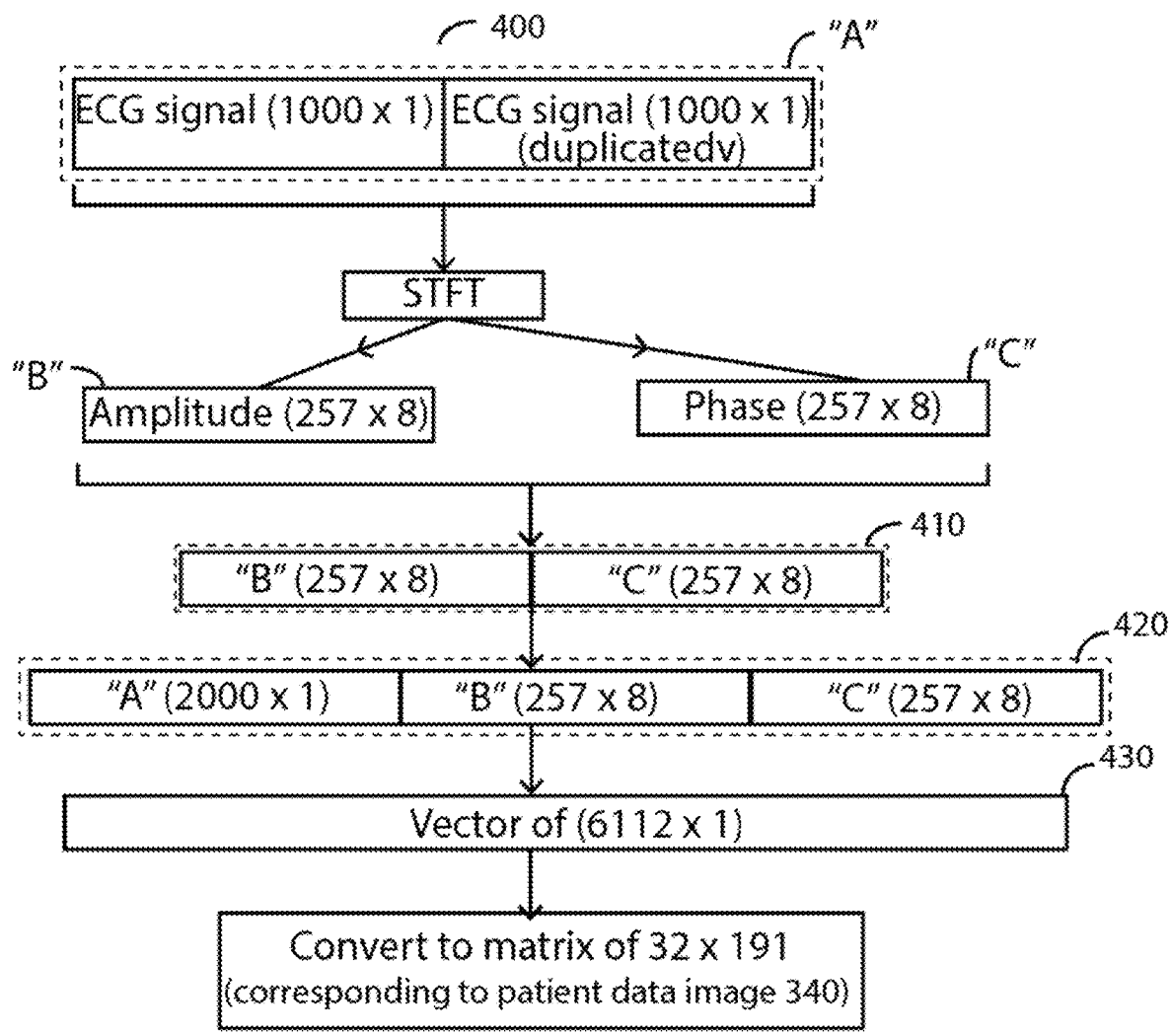
FIG. 4 depicts a method of patient data image generation in an AED according to one practice of the invention.

FIG. 4 depicts an example of generation of a patient data image in an AED according to one practice of the invention. Here 1000 samples that have been sampled, interpolated and/or extrapolated from eight-second intervals of the patient ECG signal 175 are processed at a time. Other embodiments may use a greater or lesser number of samples, representing longer or shorter intervals of time.

As shown at the top of the drawing, a vector containing 1000 samples of the patient ECG signal 175 is duplicated and appended to itself to form vector "A". The resultant vector 400 is passed to a short-time Fourier transform function STFT, though, other transforms suitable for identifying a frequency domain representation of the ECG signal 175 can be used instead or in addition, as is within the ken of those skilled in the art in view of the teachings hereof. In the illustrated embodiment, the transform (STFT) returns magnitudes and phases of each of eight (8) components of the respective frequency-domain representations of each of 257 respective time-slices of the ECG signal, with a Hamming window with 50% overlap, though other embodiments may vary in regard to these specific dimensions.

As shown in the drawing, this results in a vector "B" comprising 257×8 magnitude components and a vector "C" comprising 257×8 respective phase components. These can be appended to one another, as shown by element 410 of the drawing and, in turn, to vector A, as shown by vector 420. Vector 420 can, in turn, be unfolded to form a single one-dimensional array that is 1×6112 elements in size, as demarked 430 in the drawing. That array can, in turn, be reshaped as a matrix of dimension 32×191, which is the patient data image 340 corresponding to patient ECG signal 175.

Those skilled in the art will appreciate that the dimensions specified in the example above are by way of example and that other embodiments may employ vectors and matrices of different sizes without deviating from the spirit hereof.

Artificial Intelligence Engine

Turning back to FIGS. 1 and 2, in step 360, processor 205 of the illustrated embodiment invokes the AI engine 310 to generate a shock recommendation from the patient data image 340 using a machine learning (ML) model 320.

In step 370, the processor 205 generates an alert, if a shock is recommended, to have the operator to stand clear of the patient and to press the actuator 150 to deliver the therapeutic shock. In some embodiments, if a shock is recommended, the processor 205 can simply signal the operator to stand clear and can deliver the shock automatically by closing switch SW. Conversely, if a shock is not recommended, the processor 205 can alert the operator of such and, in some embodiments, additionally block closing of the switch SW so as to prevent application of a therapeutic shock.

Returning to discussion of step 360, the ML model 320 provides parameters (e.g., weights and biases) for use by the AI engine 310 in making the shock recommendation per convention in the art as adapted in accord with the teachings hereof. Those parameters are established during training of the model 320 with training data images 230 generated in the same manner (and format) as the patient data image 340.

Whereas the patient data image is generated by the AED 100 during a resuscitation, creation and training of the model 320 typically occurs beforehand, during a training phase, that is typically (though not necessarily) effected on a separate "training" digital data processor 250 of FIG. 1 (e.g., a mainframe computer, workstation or other digital data processor) that typically operates independently of AED 100 but from which the model 320 is downloaded or otherwise transferred following training, e.g., via a network or other communications link 260 (e.g., the Internet, a wide area network, metropolitan area network, local area network, all by way of non-limiting example, or any combination thereof), all per convention in the art as adapted in accord with the teachings hereof.

It will be appreciated that, whereas the AI engine 310 is utilized within AED 100 during a resuscitation to generate a shock recommendation using the model 320, the same engine 310 is used during the training phase to train that model 310. And, while a single common AI engine 310 and ML model 320 can be concurrently shared between the AED 100 and the training processor 250, as a practical matter, separate instantiations of that engine 310 and model 320 are copied between the respective devices. While those copies can be functionally identical, that maintained on the AED 100 can be adapted for mission-critical field use and need not include a training mode, while that on training processor 250 can be adapted for model training. In the discussion that follows common reference numerals 310 and 320 are used for the AED-based and training processor-based instantiations of the AI engine or ML model, respectively.

Although potentially presenting regulatory hurdles, in some embodiments, training and runtime phases can be combined in a single device, e.g., as where an operator of AED 100 places the onboard AI engine 310 in training mode following a defibrillation attempt and inputs to it an indication of success of the resuscitation, which the engine 310 then feeds-back to the model 320 for updating per convention in the art as adapted in accord with the teachings hereof.

AI engine 310 of AED 100 is implemented in software that is stored in memory 220 and executed on processor 205 per convention in the art as adapted in accord with the teachings hereof. AI engine 310 of training processor 250 is likewise implemented in software stored in memory 280 (which may comprise any or a combination of random-access memory (RAM), flash memory, solid state or inertial disks, or otherwise) and executed on processor 270 (which may comprise a microprocessor, FPGA, digital signal processor (DSP) or other suitable logic), again, per convention in the art as adapted in accord with the teachings hereof. In other embodiments, the engine 310 may be executed in a special-purpose processor or other logic that is separate from processor 205 and/or processor 280 but that is in communications coupling therewith, e.g., via a backplane bus or otherwise, all as is within the ken of those skilled in the art in view of the teachings hereof. ML model 320 used by the AED 100 and training processor 250, respectively, can be maintained in memory 220 and 270, respectively, for access by the local instantiation of the AI engine 310 during runtime and training operations, respectively, again per convention in the art as adapted in accord with the teachings hereof.

In embodiments, as shown here, where the engine 310 and model 320 are depicted as independent components within the AED 100, the engine can comprise a framework (or "toolkit") that defines an architecture for analysis of data images, and model 320 provides parameters (e.g., weights and biases), learned from training, for use in that architecture in providing such analysis, all per convention in the art as adapted in accord with the teachings hereof. In embodiments where the engine 310 and model 320 are integrally combined (whether or not referred to as such), they can comprise a unitary software code block (or otherwise) that both defines an architecture for image analysis and embodies trained and/or trainable such parameters, as is within the ken of those skilled in the art in view of the teachings hereof.

EXAMPLE

Figure 5:
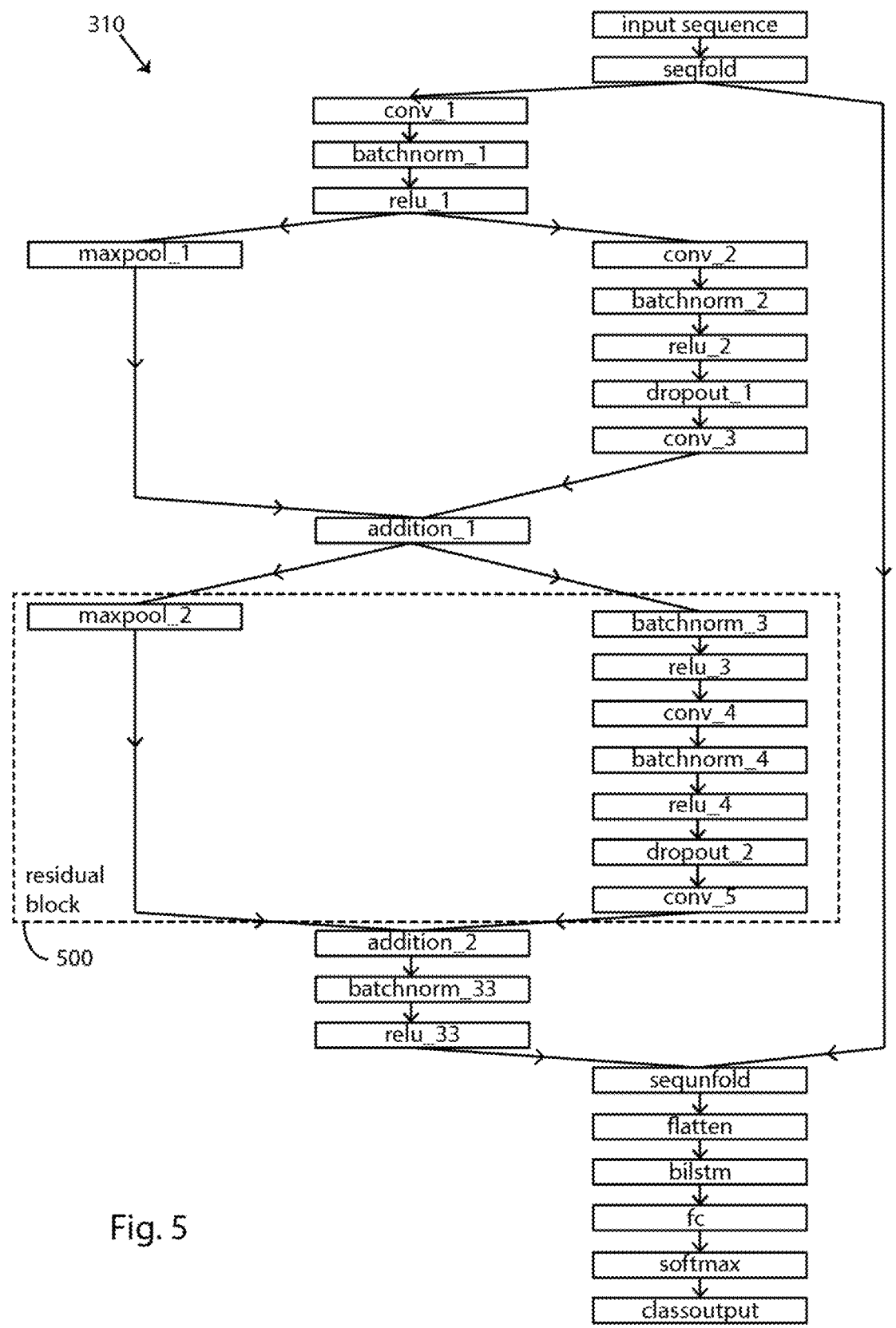
FIG. 5 depicts the architecture of an AI engine used in practice of the invention.

FIG. 5 depicts the architecture of an AI engine 310 according to one practice of the invention. The ML model 320, to which the engine 310 is coupled and on which it relies for weights, biases and other parameters to make shock recommendations, is not shown in FIG. 5.

Input to the engine 310 is provide at the layer labelled "input sequence" in the drawing, which can be a patient data image 340 in the case of engine 310 executing on AED 100 during a resuscitation or a training data image 230 in the case of engine 310 executing on training processor 250 during the training phase. The recommendation of the engine 310, which can be a shock or no-shock value, is output at the layer labelled "class output" in the drawing. In the case of engine 310 executing on AED 100, this can inform main processor 205 whether to alert the operator to stand clear of the patient and to press the actuator 150 to deliver the therapeutic shock or, in some embodiments, to so alert the operator and to close switch SW directly to deliver the shock automatically. In the case of engine 310 executing on training processor 250 during the training phase, comparison of that recommendation with known characteristics of the heart rhythm represented by the training data image (e.g., as to whether that rhythm is shockable or not) can inform further training of the model 320, all per convention in the art as adapted in accord with the teachings hereof.

AI engine 310 of the illustrated embodiment comprises a deep neural network (DNN) that includes a plurality of convolution layers (each labelled "conv_x", where x is an integer value in the drawing), although it will be appreciated that AI engines having other basic architectures, whether DNNs or otherwise, may be used in practice of the invention.

The illustrated AI engine 310 includes a bidirectional long short-term memory layer (labelled "biLSTM" in the drawing) in sequence with the convolution layers, although (again) it will be appreciated that AI engines of other morphologies may be used instead or in addition.

Moreover, AI engine 310 of the illustrated embodiment includes a residual connection layer in sequence with the convolution layers and the biLSTM layer, though, again other embodiments may vary in this regard.

As shown in the drawing, a preferred AI engine 310 can comprise one or more residual blocks—as designated, here, by the dashed-line box labelled 500—each including multiple convolutional layers.

With further reference to FIG. 5, the architecture of the illustrated engine 310, is comprised of multiple processing layers consisting sequentially of a CNN, BiLSTM architecture of the type known in the art (see, for example S. Hochreiter and J. Schmidhuber "Long Short-Term Memory," Neural Computation, vol. 9, no. 8, pp. 1735-1.780 November 1997, doi: 10.1162/neco.1997.9.8.1735)) as adapted in accord with the teachings hereof, and a residual connection layer of the type known in the art (see, for example, K. He, X. Zhang, S. Ren, and J. Sun, "Identity Mappings in Deep Residual Networks," arXiv:1603.05027 [cs], July 2016) as adapted in accord with the teachings hereof. Residual blocks with two CNN architectures are employed in each block. Those residual blocks are of the type know in the art (see, for example, "Cardiologist-Level Arrhythmia Detection in ECGs using a Deep Neural Network." https://stanfordmlgroup.github.io/projects/ecg2/) as adapted in accord with the teachings hereof.

During the training phase, a default initialization, consisting of random weights, is applied. The CNN layers have filter dimensions of 16×32×1, 16×32×2, and 16×32×4, for 1st to 4th, 5th to 8th and 9th to 12th convolutional layers, respectively. There are dropout layers with a probability of 0.4 before each CNN layer. The final layers include BiLSTM and fully connected layers in addition to the Softmax function layer, to produce the classification results. The adaptive moment estimation (Adam) optimizer with default parameters of $\beta_1=0.9$, $\beta_2=0.999$ and a mini batch size of 128 is used. An initial learning rate of 0.001 is used, and it decreased every 4 epochs by the drop factor of 0.1. To make a better shock decision based on 8-second samples of ECG data, manual tuning of hyper-parameters such as the number of layers, the number of residual blocks, and the number of iterations can be performed, and a final set of parameters chosen based on best fit.

With further reference to the drawing, the function of the respective layers of the illustrated AI engine 310 may be appreciated by reference to the table below.

TABLE 1

| LAYER NAME | TYPE | ACTIVATIONS |
| --- | --- | --- |
| Input sequence | Sequence Input | 32 × 191 × 1 |
| seqfold | Sequence Folding | out 32 × 191 × 1 |
| | | miniBatchSize 1 |
| conv_1 | Convolution | 32 × 191 × 16 |
| batchnorm_1 | Batch Normalization | 32 × 191 × 16 |
| relu_1 | ReLU | 32 × 191 × 16 |
| maxpool_1 | Max Pooling | 32 × 191 × 16 |
| conv_2 | Convolution | 32 × 191 × 16 |
| batchnorm_2 | Batch Normalization | 32 × 191 × 16 |
| relu_2 | ReLU | 32 × 191 × 16 |
| dropout_1 | Dropout | 32 × 191 × 16 |
| conv_3 | Convolution | 32 × 191 × 16 |
| addition_1 | Addition | 32 × 191 × 16 |

TABLE 1-continued

| LAYER NAME | TYPE | ACTIVATIONS |
|---|---|---|
| maxpool_2 | Max Pooling | 32 × 191 × 16 |
| batchnorm_3 | Batch Normalization | 32 × 191 × 16 |
| relu_3 | ReLU | 32 × 191 × 16 |
| conv_4 | Convolution | 32 × 191 × 16 |
| batchnorm_4 | Batch Normalization | 32 × 191 × 16 |
| relu_4 | ReLU | 32 × 191 × 16 |
| dropout_2 | Dropout | 32 × 191 × 16 |
| conv_5 | Convolution | 32 × 191 × 16 |
| addItIon_2 | Addition | 32 × 191 × 16 |
| batchnorm_33 | Batch Normalization | 32 × 191 × 16 |
| relu_33 | ReLU | 32 × 191 × 16 |
| sequnfold | Sequence Unfolding | 32 × 191 × 16 |
| flatten | Flatten | 97792 |
| bilstm | BiLSTM | 256 |
| fc | Fully Connected | 2 |
| softmax | Softmax | 2 |
| classoutput | Classification Output | — |

Residual Blocks

To determine an optimal number of residual blocks 50 used in the AI engine 310 of FIG. 5 for patient image data and training image data generated as discussed herein, data from 40 subjects' ECGs and 43 rescuers' CPR samples with a 4-fold cross validation scheme were used to generate 28,887 non-shockable and 19,227 shockable 8-second training data segments with and without CPR artifact test data sets in the manner described below, though for purposes of determining an optimal number of residual blocks 12,441 non-shockable and 12,441 shockable of these were used as the training data, and 16,446 non-shockable and 6,786 shockable 8 second segments as the "patient" data.

The AI engine 310 of FIG. 5 was trained and tested using both shockable and non-shockable ECG data with and without CPR artifact using 4-fold cross validation by varying the number of residual blocks 500 starting from one to six at an increment of one. Note that each block 500 contained two CNN layers. In addition, there was a single CNN layer at the beginning of the DNN architecture, thus, in Table 2, below we show the total number of CNN layers for our choice of one to six residual blocks. The results shown in Table 2 were based on the summation of all true positive (TPs), true negative (TNs), false positive (FPs), and false negative (FNs) from the 4-fold cross-validation. TP is the correct classification of shockable, TN is the correct classification of non-shockable, FP is the incorrect classification of non-shockable as shockable and FN is the incorrect classification of shockable as non-shockable. Note that the number of iterations is the same for training all six cases of residual blocks.

TABLE 2

| Number of Res blocks | Number of CNN Layers | Sensitivity | Specificity | Accuracy | F1-score |
|---|---|---|---|---|---|
| 1 | 2 | 90.72% | 88.23% | 88.96% | 82.76% |
| 2 | 5 | 92.40% | 86.20% | 87.30% | 80.04% |
| 3 | 7 | 93.50% | 87.22% | 88.10% | 82.20% |
| 4 | 9 | 95.21% | 86.03% | 88.13% | 83.52% |
| 5 | 11 | 95.52% | 83.37% | 86.22% | 80.39% |
| 6 | 13 | 94.50% | 84.11% | 86.00% | 80.10% |

As shown in Table 2, an engine 310 with four residual blocks 500 with nine CNN layers provided better classification results. Therefore, this can be an optimal choice for some embodiments, as increasing the number of residual blocks up to six (13 CNN layers) does not necessarily further improve performance, yet, may come at the expense of higher computational costs.

Training Data Sets

ML model 320 is trained with training data images 230 generated in the same manner and format as the patient data image 340, albeit from sets of training data. In the illustrated embodiment, the training phase that is carried out on training digital data processor 250; although, in some embodiments, it can be carried out on the AED 100, instead or in addition.

Each set of training data comprises ECG data representing the electrical activity of the heart of a person (e.g., a test subject, a heart attack victim, or other) who is undergoing CPR while experiencing (i) ventricular fibrillation (VF), pulseless ventricular tachycardia (VT), or other shockable rhythm, or (ii) normal sinus rhythm (NSR), atrial fibrillation (AF), sinus bradycardia (SB), supraventricular tachycardia (SVT), heart block, idioventricular and premature ventricular contractions (PVCs) or other non-shockable rhythms. At least some training data sets also comprise ECG representing electrical activity of the hearts of persons experiencing such shockable or non-shockable rhythms but that are not undergoing CPR.

In addition to the ECG data representing the electrical activity of a subject's heart and that may include artifacts resulting from CPR, each training data set includes an identifier (or classification) indicating whether the underlying heart rhythm was shockable or non-shockable. That identifier can be based on post facto situational analysis (e.g., analysis of whether a shock was or was not, in fact, delivered to the subject and whether it was successful in placing him/her back into NSR), post facto data analysis (e.g., human expert or other of the ECG data to discern the nature of the underlying heart rhythm), or otherwise as is within the ken of those skilled in the art in view of the teachings hereof.

In some embodiments, training data sets comprise ECG signals (and indicators or classification, e.g., shockable/non-shockable) collected during defibrillation procedures (by AED 100 or otherwise) during the course of patient resuscitations. Alternatively, or in addition, in some embodiments, like those discussed below each set of training data is synthesized from (i) an ECG signal collected from a subject who was not undergoing CPR when that respective signal was collected, and (ii) an ECG signal collected from the same or another subject who was in asystole and was undergoing CPR when that respective signal was collected. The former is referred to below as "ECG data" and the latter is referred to as "CPR data."

By combining—and, particularly in the illustrated embodiment, summing—those two ECG signals (i.e., the ECG data and CPR data), training processor 250 can create a training data set representing training ECG signals (also referred to here as training ECG data) as if collected from a subject undergoing CPR while not in asystole.

In the illustrated embodiment, summation or other combination of the ECG signals is performed on their time-series forms (hence, reference to those ECG signals as ECG "data"); though, other embodiments may vary in this regard (e.g., by combining frequency-domain representations and converting them back to the time domain, or using the frequency-domain representation directly for training data image generation).

Figure 6:
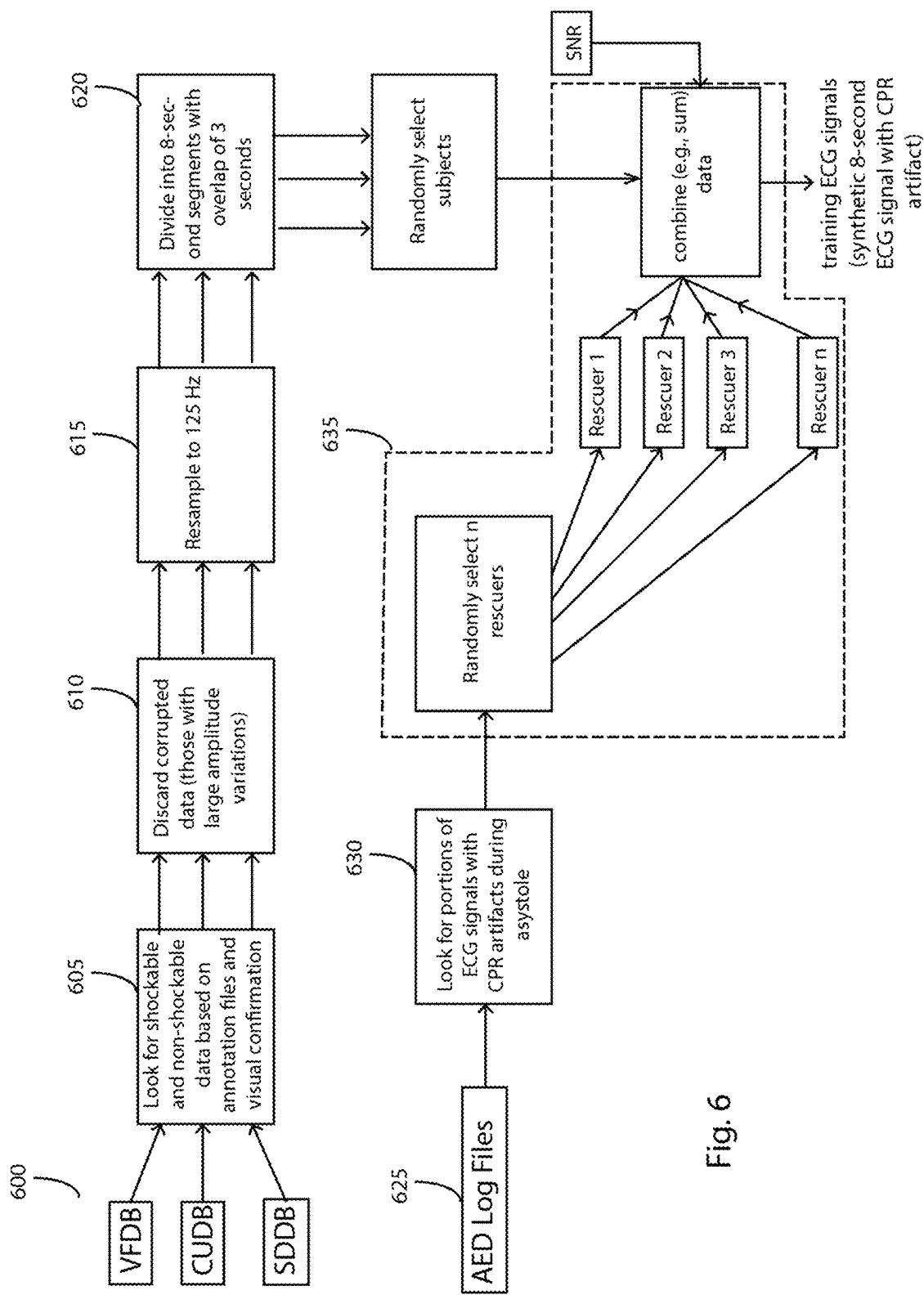
FIG. 6 depicts a method of generating training ECG signals by combining (e.g., summing) ECG data and "CPR" data in a system according to the invention.

Discussed in the example below is a method according to the invention of generating a robust set of such training data from databases, e.g., of ECG data (i.e., ECG signals collected from subjects who were not undergoing CPR when the respective signals were collected) and CPR data (i.e., ECG signals collected from subjects who were in asystole and were undergoing CPR when the respective signals were collected). It will be appreciated that the method discussed below and shown in FIG. 6 is merely an example and that training ECG signals can be generated in other ways, e.g., as discussed above and as within the ken of those skilled in the art in view of the teachings hereof. Thus, for example, although ECG data and CPR data used to generate training data in the example below are understood to be from adult subjects, in other embodiments such data can include that from pediatric subjects, as well, thus, enabling training of a model 320 that can better accommodate patients of both age ranges.

EXAMPLE

Referring to FIG. 6, step 600, ECG recordings were accessed from the Creighton University tachyarrhythmia database ("CUDB"), MIT-BIH malignant ventricular arrhythmia database ("Ng:DB"), and the sudden cardiac death Holter database ("SDDB") per convention in the art as adapted in accord with the teachings hereof. Those recordings have a sampling frequency of 250 Hz with 12-bit resolution over a 10-millivolt range. The CUDB, VFDB, and SDDB databases contain recordings from 35, 22 and 18 subjects, respectively.

In step 605, visual representations of the aforesaid ECG recordings and accompanying annotation files were reviewed to identify recordings that contained either shockable (VF or fast VT) or non-shockable arrhythmias. Recordings with short duration were discarded. Step 610. Recordings of 20 subjects from CUDB, 10 from VFDB, and 10 from SDDB remained following the culling. These were resampled to 125 Hz (step 615) and used in the steps that follow. Thirty subjects had both shockable and non-shockable rhythms. The remaining 10 subjects had only non-shockable rhythms. As used herein, the term "clean ECG" refers to those recordings which do not contain CPR artifacts.

In step 620, the resampled ECG recordings were divided into 8-second segments with overlap of 3 seconds. This resulted in 1,131 shockable (285 from CUDB, 576 from VFDB, and 270 from SDDB) and 2,741 non-shockable (877 from CUDB, 973 from VFDB, and 891 from SDDB) segments. A preprocessing step (not shown) consisted of band-pass filtering ([0.4 30] Hz) and removing the mean value of each data segment. The signal-to-noise ratio of the combined data was −3 dB.

Figure 7:
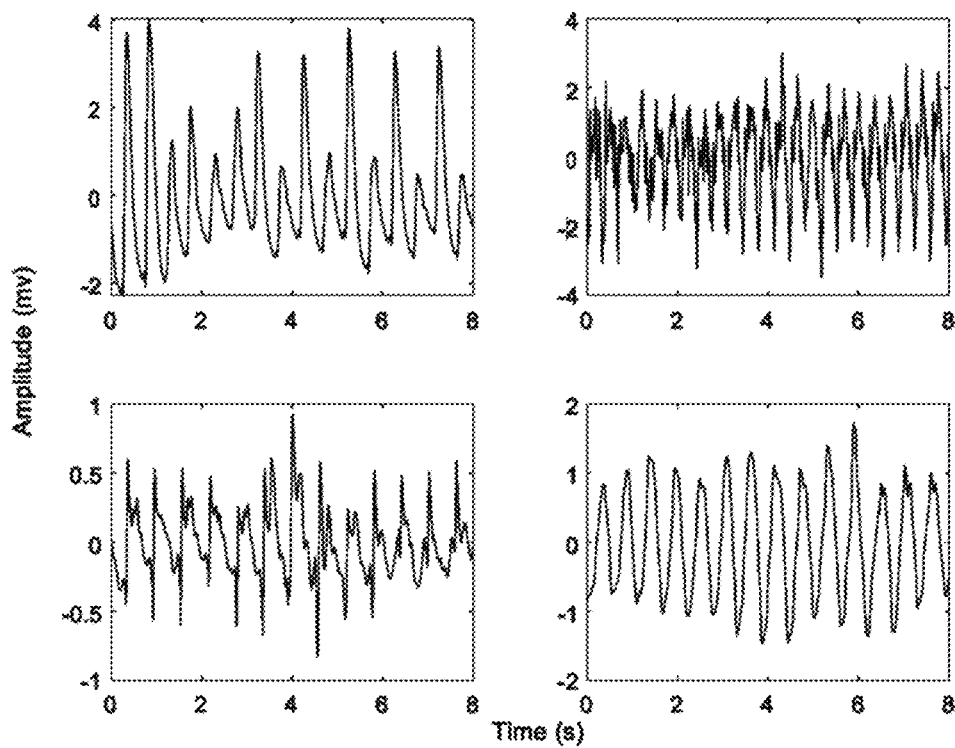
FIG. 7 depicts samples of CPR data from a CPR artifact database used in practice of the invention.

In step 625, ECG recordings contained in log files of AEDs available in the marketplace that had been used on patients and/or test subjects were accessed. Recordings were selected that showed CPR artifacts during asystole. Step 630. Since the amplitude of ECG during asystole is negligible, the ECG signals in these regions of the recordings largely represent only CPR artifacts (i.e, electrical activity that is the result of CPR, not of heart rhythm). The sampling frequency of the recordings from the AEDs was 125 Hz. The CPR artifacts they embodied were diverse as they were obtained from 43 different rescuers. Following step 620, there were 43 recordings of CPR artifacts. FIG. 7 depicts samples of those ECG signals (or "CPR data") from four different rescuers. Note the high variability of CPR artifacts in terms of their amplitudes and frequencies Referring back to FIG. 6, to each 8-second ECG segment generated in step 620, randomly chosen CPR data was combined by way of time-wise summation from the total of 43 different types of CPR data generated in step 630 so that 5 non-shockable and 10 shockable CPR-contaminated ECG data segments were created from each 8-second ECG segment. Step 635.

A greater number of CPR types for shockable rhythms than non-shockable were chosen since there were more available non-shockable data. In this manner, more balanced datasets from both shockable and non-shockable rhythms were obtained. Hence, 11 samples (including 10 CPR-contaminated samples and 1 clean sample) were generated for each shockable ECG, and 6 samples (including 5 CPR-contaminated samples and 1 clean sample) for every non-shockable ECG. Generating test data sets containing both CPR-contaminated ECG and clean ECG samples ensured that the AED 100 could automatically make shock/no shock decisions regardless of whether patient data contained only the ECG itself or ECG with CPR. This also enables training the ML model 320 to make a decision on shockable versus non-shockable without any prior knowledge regarding the presence or absence of CPR.

Figure 8:
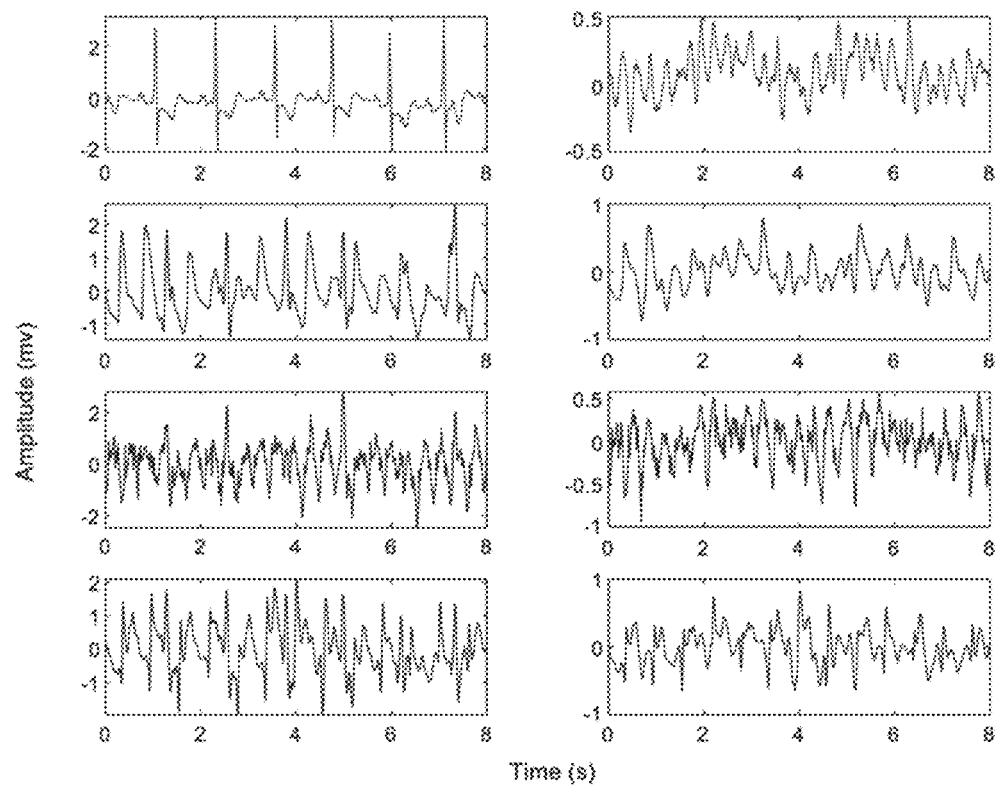
FIG. 8 depicts a combination of CPR artifacts with normal sinus rhythm and ventricular fibrillation rhythms in accord with practice of the invention.

FIG. 8 depicts a few of the aforesaid combinations, more particularly, time-wise summations, of assorted CPR artifact recordings (from the CPR database) with either normal sinus rhythm (NSR: left panels) or ventricular fibrillation recordings (VF: right panels) (from the ECG databases). The top row of the left and right columns represents NSR and VF, respectively, both without CPR artifact. The remaining rows of the left and right columns represent three different CPR artifacts combined with clean NSR and VF, respectively. In most cases, the CPR artifact is the dominant signal with only faint tracings of either the NSR or VF rhythms superimposed on top of the CPR dynamics.

Training the ML Model

In the illustrated embodiment, the training ECG signals (e.g., generated in step 635 or otherwise) are used to generate training data images with which the AI engine is invoked to generate shock recommendations using the ML model 320 and, in turn, to train that model 320 via a methodology that parallels that shown in FIG. 2 and discussed above in connection therewith, with the following caveats:

- Training ECG signals generated as discussed above are converted to time-series form, if not already in that form following step 635.
- Training is performed on training digital data processor 250, not AED 100; though, other embodiments may vary in this regard.
- For purposes of training the ML model 320, steps 300 are implemented by way of instructions/data stored in memory 280 and executed on processor 270, all per convention in the art as adapted in accord with the teachings hereof.
- For purposes of training the ML model, step 330 receives each training ECG signal from memory 280 following its generation as discussed above e.g., in step 635. Unlike execution of step 330 by the AED during a resuscitation, this need not be in real-time.
- For purposes of training the ML model, step 340 is invoked to generate a training data image from each training ECG signal.
- For purposes of training the ML model, in step 360, processor 270 invokes the AI engine 320 to generate a shock recommendation.
- For purposes of training the ML model, in lieu of executing step 370 to generate an alert and/or a shock, the processor 270 compares the shock recommendation generated by the AI engine 310 in step 360 with classification (i.e., shockable or non-shockable) of the ECG data from which the training ECG signal was generated in steps 600-635. If the compared values do not match, the AI engine 310 feeds that classification back to the model 320 for updating per convention in the art as adapted in accord with the teachings hereof.

Described herein are apparatus and methods meeting the objects set forth above. It will be appreciated that the embodiments shown in the drawings and discussed above are merely examples and that other embodiments incorporating changes thereto fall within the scope of the invention. Thus, by way of non-limiting example, although patient ECG signals and training ECG signals used in the examples discussed above were eight seconds in duration, it will be appreciated such signals processed in other embodiments may be of other durations, e.g., for example, between five and fifteen seconds. Moreover, it will be appreciated that, although the embodiments discussed above are directed to automated external defibrillation, it will be appreciated that many of the teachings hereof are equally applicable to other health care devices and techniques.

In view of the foregoing, what we claim is:

1. An automated external defibrillator (AED), comprising:
   A. defibrillation circuitry capable of delivering a therapeutic shock to a patient,
   B. an input that receives a patient ECG signal representing real-time electrical activity of a heart of the patient and that may include artifacts resulting from cardiopulmonary resuscitation of the patient,
   C. an artificial intelligence (AI) engine that generates a shock recommendation from a patient data image that is based on the patient ECG signal using a machine learning (ML) model trained with training data images, the patient data image comprising pixels whose values are a function of magnitudes of components of representations of respective time-slices of the patient ECG signal in a frequency domain, and at least one training data image comprising pixels whose values are a function of magnitudes of respective components of representations of respective time-slices of a respective training ECG signal in the frequency domain, and
   D. the AED generating a real-time alert to effect application of the therapeutic shock to the patient, where the AED generates that real-time alert based at least in part on the shock recommendation of the AI engine.

2. The automated external defibrillator of claim 1, wherein
   A. the patient data image comprises pixels whose values are a function of phases of components of the representation of the respective time-slice of the patient ECG signal in the frequency domain, and
   B. the at least one training data image comprises pixels whose values are a function of phases of the components of the representation of the respective time-slice of the respective training ECG signal in the frequency domain.

3. The automated external defibrillator of claim 1, wherein
   A. the patient data image comprises pixels whose values are a function of amplitudes of respective sampled values of a representation of the patient ECG signal in a time domain, and
   B. the at least one training data images comprises pixels whose values are a function of amplitudes of respective sampled values of a representation of the respective training ECG signal in the time domain.

4. The automated external defibrillator of claim 1, wherein

A. the patient data image comprises a plurality of regions, each comprising at least a two-dimensional collection of 500 or more pixels,
      where the plurality of regions includes at least two of
      (a) a region comprising pixels whose values are a function of magnitudes of components of the representation of the respective time-slice of the patient ECG signal in the frequency domain,
      (b) a region comprising pixels whose values are a function of phases of components of the representation of the respective time-slice of the patient ECG signal in a frequency domain,
      (c) a region comprising pixels whose values are a function of amplitudes of respective sampled values of the representation of the patient ECG signal in the time domain, and
   B. the at least one training data images comprises a plurality of regions, each comprising at least a two-dimensional collection of 500 or more pixels,
      where the plurality of regions includes at least two of
      (a) a region comprising pixels whose values are a function of magnitudes of respective components of the representation of a respective time-slice of a respective training ECG signal in the frequency domain,
      (b) a region comprising pixels whose values are a function of phases of respective components of the respective representation of the respective time-slice of the respective training ECG signal in the frequency domain,
      (c) a region comprising pixels whose values are a function of amplitudes of respective sampled values of a representation of the respective training ECG signal in the time domain.

5. The automated external defibrillator of claim 1, wherein
   A. at least one training ECG signal is derived from a summation of (i) a time series of ECG data of collected from a subject who was not undergoing CPR when that data was collected, and (ii) a time series of ECG data collected from a subject in asystole and undergoing CPR when that data was collected,
   B. the training ECG signal represents ECG data as if collected from the subject undergoing CPR while not in asystole.

6. The automated external defibrillator of claim 1, wherein the ML model is trained using (a) a first plurality of training data sets derived from a said summation in which the training ECG data is collected from subjects whose hearts were in a shockable rhythm, and (b) a second plurality of training data sets derived from a said summation in which the ECG data was collected from subjects whose hearts were not in a shockable rhythm.

7. The automated external defibrillator of claim 5, in which each summation training data set is 5-15 seconds in length.

8. The automated external defibrillator of claim 1, wherein the AI engine comprises a deep neural network (DNN) that includes a plurality of convolution layers.

9. The automated external defibrillator of claim 8, wherein the DNN includes a bidirectional long short-term memory (biLSTM) layer in sequence with the convolution layers.

10. The automated external defibrillator of claim 9, wherein the DNN includes a residual connection layer in sequence with the convolution layers and the biLSTM layer.

11. The automated external defibrillator of claim 10, wherein the DNN includes plural residual blocks, each including multiple convolutional layers.

12. A method of automated external defibrillation, comprising
   A. receiving a patient ECG signal representing real-time electrical activity of a heart of a patient and that may include artifacts resulting from cardiopulmonary resuscitation of the patient,
   B. generating a patient data image from pixels whose values are a function of magnitudes of components of representations of respective time-slices of the patient ECG signal in a frequency domain,
   C. generating a real-time alert to effect application of a therapeutic shock to the patient by determining an efficacy of applying such a shock by analyzing the patient data image with an artificial intelligence (AI) engine and a machine learning (ML) model trained with training data images whose pixel values are a function of magnitudes of respective components of representations of respective time-slices of respective training ECG signals in the frequency domain.

13. A method of claim 12, comprising
   A. generating the patient data image with pixels whose values are a function of phases of components of the representations of the respective time-slices of the patient ECG signal in the frequency domain, and
   B. using, to analyze the patient data image, training data images that comprise pixels whose values are a function of phases of the components of the respective representations of the respective time-slices of the respective training ECG signals in the frequency domain.

14. A method of claim 12, comprising
   A. generating the patient data image with pixels whose values are a function of amplitudes of respective sampled values of a representation of the patient ECG signal in a time domain, and
   B. using, to analyze the patient data image, training data images that also comprise pixels whose values are a function of amplitudes of respective sampled values of representations of the respective training ECG signals in the time domain.

15. A method of claim 12, comprising
   A. generating the patient data image with a plurality of regions, each comprising at least a two-dimensional collection of 500 or more pixels, where the plurality of regions includes at least two of
      (a) a region comprising pixels whose values are a function of magnitudes of components of representations of respective time-slices of the patient ECG signal in the frequency domain,
      (b) a region comprising pixels whose values are a function of phases of components of the representations of respective time-slices of the patient ECG signal in the frequency domain,
      (c) a region comprising pixels whose values are a function of amplitudes of respective sampled values of the representation of the patient ECG signal in the time domain, and
   B. using, to analyze the patient data image, training data images that comprises a plurality of regions, each comprising at least a two-dimensional collection of 500 or more pixels, where the plurality of regions includes at least two of
      (a) a region comprising pixels whose values are a function of magnitudes of respective components of representations of a respective time-slices of respective training ECG signals in the frequency domain,
      (b) a region comprising pixels whose values are a function of phases of the respective components of the respective representations of the respective time-slices of the respective training ECG signals in the frequency domain,
      (c) a region comprising pixels whose values are a function of amplitudes of respective sampled values of a representation of the respective training ECG signal in the time domain.

16. A method of claim 12, comprising training the ML model training ECG signals that are summations of (i) time series of ECG data collected from respective subjects who were not undergoing CPR when that respective data was collected, and (ii) time series of ECG data collected from the same or other subjects who were in asystole and who were undergoing CPR when that respective data was collected, which ECG signals represent ECG data as if collected from the respective subject undergoing CPR while not in asystole.

17. A method of claim 12, wherein step (C) includes analyzing the patient data image with a deep neural network (DNN) that includes a plurality of convolution layers.

18. A method of claim 17, wherein step (C) includes analyzing the patient data image with the deep neural network that includes a bidirectional long short-term memory (biLSTM) layer in sequence with the plurality of convolution layers.

19. A method of claim 18, wherein step (C) includes analyzing the patient data image with the deep neural network that includes a residual connection layer in sequence with the convolution layers and the biLSTM layer.

20. A method of claim 17, wherein step (C) includes analyzing the patient data image with the deep neural network that includes plural residual blocks, each including multiple convolutional layers.

* * * * *